United States Patent [19]

Papritz et al.

[11] Patent Number: 5,134,515
[45] Date of Patent: Jul. 28, 1992

[54] PHOTOGRAPHIC ATTACHMENT AND SHUTTER DEVICE FOR A BINOCULAR MICROSCOPE

[75] Inventors: Franz Papritz; Hansruedi Widmer, both of Niederscherli, Switzerland

[73] Assignee: Haag-Streit AG, Switzerland

[21] Appl. No.: 613,788

[22] PCT Filed: May 10, 1990

[86] PCT No.: PCT/CH90/00126

§ 371 Date: Jan. 4, 1991

§ 102(e) Date: Jan. 4, 1991

[87] PCT Pub. No.: WO90/13255

PCT Pub. Date: Nov. 15, 1990

[30] Foreign Application Priority Data

May 11, 1989 [EP] European Pat. Off. ........ 89810350.2

[51] Int. Cl.⁵ ............................................ G02B 21/36
[52] U.S. Cl. .................................. 359/223; 359/225; 359/363; 359/369; 359/862
[58] Field of Search ............... 350/354, 502, 507, 508, 350/511, 574, 623; 359/223, 225, 226, 241, 363, 368, 369, 372, 503, 862, 863

[56] References Cited

U.S. PATENT DOCUMENTS

| | | | |
|---|---|---|---|
| 3,141,396 | 7/1964 | Kimball | 95/11 |
| 3,533,342 | 10/1970 | McMillin | 98/18 |
| 3,820,882 | 6/1974 | Jakubowski | 352/131 |
| 4,143,938 | 3/1979 | Feinbloom | 350/19 |
| 4,174,159 | 11/1979 | Kraft et al. | 354/23 R |
| 4,206,966 | 7/1980 | Tyson et al. | 350/19 |
| 4,265,518 | 5/1981 | Matsumura | 351/7 |
| 4,302,087 | 11/1981 | Reinheimer et al. | 354/79 |
| 4,527,869 | 7/1985 | Nihoshi | 350/502 |
| 4,594,608 | 6/1986 | Hatae et al. | 358/93 |

FOREIGN PATENT DOCUMENTS 2040155 8/1970 Fed. Rep. of Germany .
1129603 1/1957 France .

Primary Examiner—Frank Gonzalez
Attorney, Agent, or Firm—Ostrolenk, Faber, Gerb & Soffen

[57] ABSTRACT

The housing (10), which is inserted between the magnification selector (7) and the ocular tube (8) of a microscope, accommodates a pivotable mirror (22) which is normally placed outside the beam path of the microscope, but which by actuating a lever (17) can be pivoted into the beam path in order to deliver the latter through a photo cone (13) to a camera (14). By actuating the lever (17), the camera (14) is released after the required chronological delay in order to take a picture of the object, e.g. an eye (4). A diaphragm arrangement, which can be brought into the preselected position for the exposure as well by actuation of the lever (17), is disposed at the entry of the housing (10), i.e. directly adjacent the magnification selector (7). Due to the full availability of the light and the advantageous position and adjustability of the diaphragm, optimum conditions exist both for observation and for photographical exposures.

16 Claims, 4 Drawing Sheets

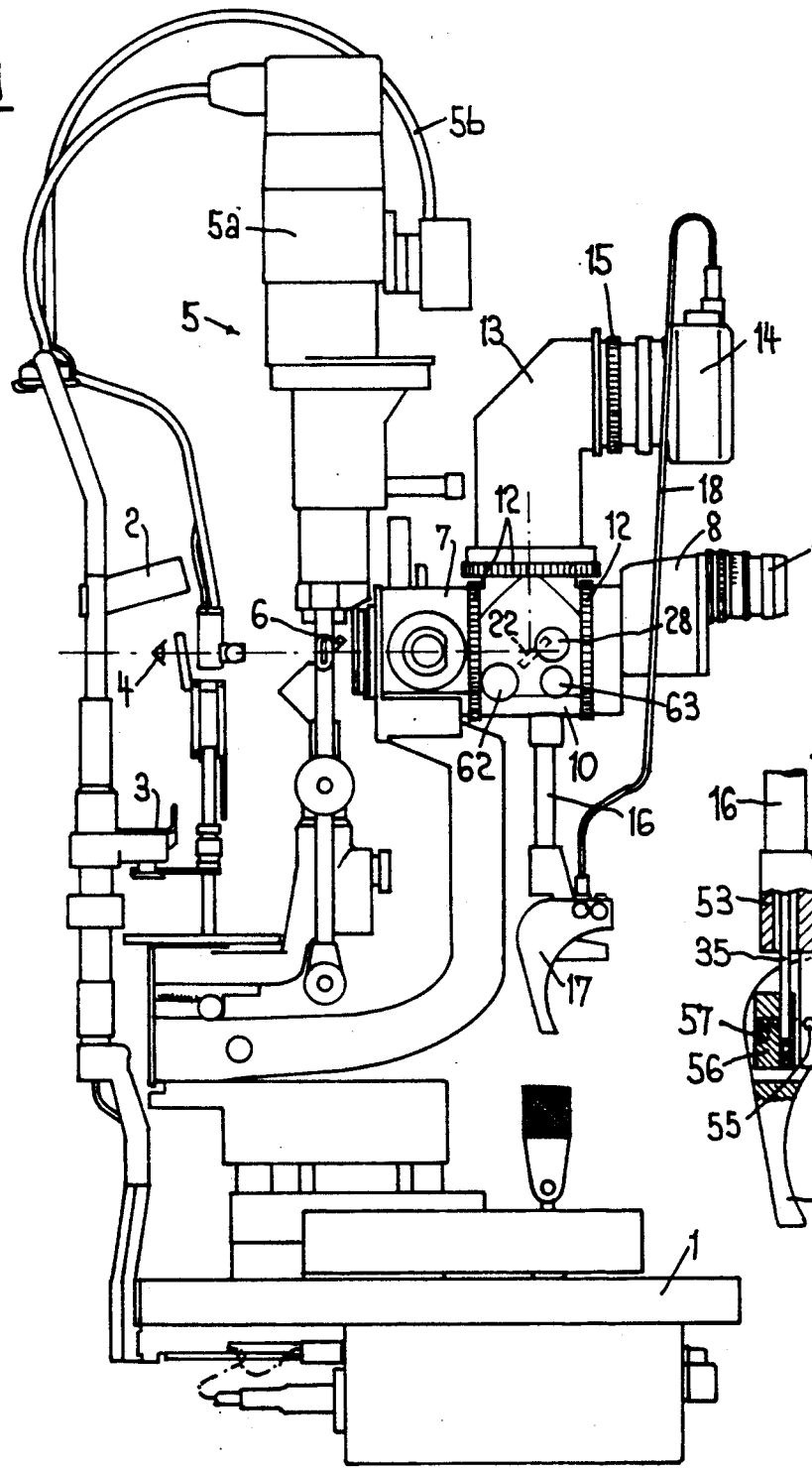

PHOTOGRAPHIC ATTACHMENT AND SHUTTER DEVICE FOR A BINOCULAR MICROSCOPE

The present invention concerns a photo supplement on a microscope, in particular an ophtalmological microscope for the observation of the eye with a slit lamp, comprising means for deviating light from the beam path of the microscope and directing it into a photo camera. Known photo supplements of this kind are provided with so-called beam splitters comprising semi-reflecting mirrors, one respective portion of the light flux of the imaging ray beam being deflected towards the photo tube with the camera while the remaining fraction reaches the oculars of the microscope. A 100% of the light flux are thus available neither for observation nor for photography, which is disadvantageous.

The present invention is based upon the object of eliminating this drawback and of creating a photo supplement in which all the available light may be used both for observation and for photographic exposures. This object is attained by providing a fully reflecting mirror which is adapted to be moved into the beam path for each photographic exposure. It is thus possible, when the mirror is located outside the beam path of the microscope, to contemplate an object, e.g. an eye, with all the available light, and then to move the mirror into the beam path for a short time and to take a photographic exposure with all the available light. Introducing the mirror into the beam path of the microscope, releasing the camera for the exposure, and returning the mirror to its rest position outside the beam path can be effected so quickly, and these operations can be operated by a single, simple manipulation, that the contemplation of the object is barely disturbed by the exposure.

Known photo supplements of the above-described kind have an adjustable iris diaphragm built into the photo tube which is connected to the beam splitter. Strong vignetting effects result from the unfavorable position of this diaphragm inside the entire imaging beam path, with the practical consequence that when using e.g. a miniature format of 24×36 mm, and depending on the selected magnification and diaphragm, more or less important marginal portions are shaded up to complete darkness. It is another object of the present invention to provide a diaphragm arrangement which prevents the drawbacks of known diaphragms. This object is attained by the fact that the diaphragm or diaphragms are placed in front of the mirror with respect to the beam path. In other words, the diaphragm is located between the mirror and the object, more particularly between the mirror and a magnification selector of the microscope.

The invention in particular also concerns a diaphragm arrangement according to the explanations above and according to claims 11 to 13, for use in a binocular microscope more particularly comprising a photo supplement. Among other things, this diaphragm arrangement is advantageous in that it may be operated in a simple manner in conjunction with the mentioned mirror, and moreover, that it may be disposed in the also mentioned favorable position. Besides, it has the advantage of influencing both beam paths of the binocular microscope in the same manner, so that any kind of camera tubes for mono, stereo or instant exposures may be used without necessitating further measures. Finally, the diaphragm arrangement is particularly simple in its construction and operation, as will be explained in more detail.

The invention is now described in more detail by means of an embodiment as illustrated in the drawing.

FIG. 1 shows a slit lamp with the photo supplement of the invention;

FIG. 2 shows a part of the operating device on an enlarged scale and in a partially sectioned view;

Figure 3:
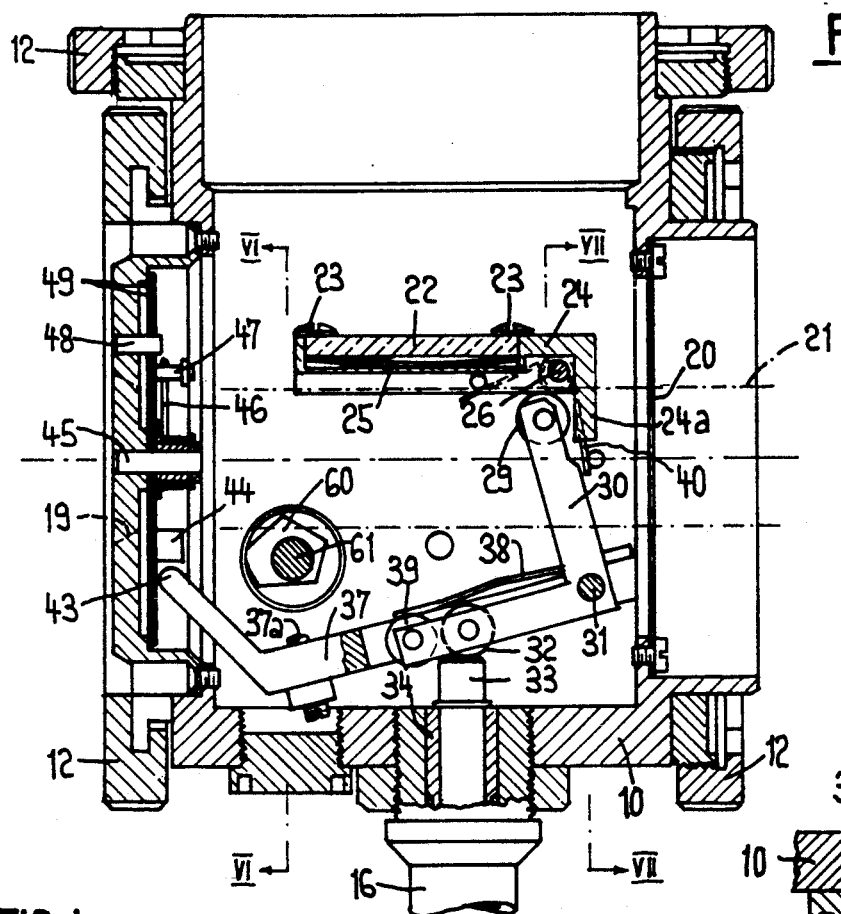
FIG. 3 shows a section of a part of the housing with the mirror and the diaphragm in their rest positions.
Figure 5:
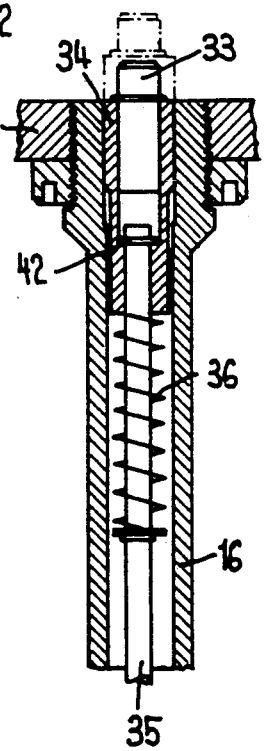
FIG. 5 shows a partial section of a control linkage.

FIG. 1 shows a slit lamp which is equipped with the photo supplement of the invention. This slit lamp is described in the pamphlet "*die neue Haag-Streit Spaltlampe 900 BQ*" of the company Haag-Streit AG, and only a few components of this slit lamp which are interesting in the context of the invention will be mentioned. The slit lamp is mounted on a base 1 and provided with a forehead rest 2 and a chin rest 3 for a patient of whom only the eye 4 is schematically shown in FIG. 1. For the observation of the eye, a slit lamp lighting 5 with a flashlight 5a is provided which allows illuminating the eye 4 via an inclined mirror 6, and optional additional devices as indicated in FIG. 1. A binocular microscope is intended for the observation of the eye, such microscope comprising a magnification selector 7 and an ocular tube 8 with the oculars 9. Between the magnification selector 7 and the ocular tube 8, a housing 10 for the photo supplement according to the invention is inserted and removably secured by means of fixing rings 12. A lens tube or photo tube 13 is attached to housing 10 by means of a fixing ring 12 as well, a miniature format camera 14 being removably connected to said photo tube 13 by means of a fixing ring 15. A tube 16 is mounted on the underside of the housing 10 and accommodates a control linkage which will be described below. Said control linkage is coupled to an operating lever 17 which serves also to trigger camera 14 via a cable 18. In the rest position of the photo supplement, the eye 4 can be observed unrestrainedly through the microscope. During the observation, the beam path of the microscope can be temporarily deflected, by operating release lever 17, through photo tube 13 to camera 14, and a picture of the eye 4 can be made by releasing camera 14. The arrangement permitting such operation is described in detail herebelow.

Housing 10 is provided with entry openings 19 and exit openings 20 for the parallel observation ray beams 21 of the binocular microscope. Housing 10 accommodates a mirror 22 which is precisely adjustable in a holder 24 by means of a leaf spring 25 urging mirror 22 against screws 23 and thus determining the position of the mirror with respect to holder 24. Holder 24 with mirror 22 is mounted on a pivot axle 26 which is journalled in the housing walls by means of ball-bearings 27

Figure 7:
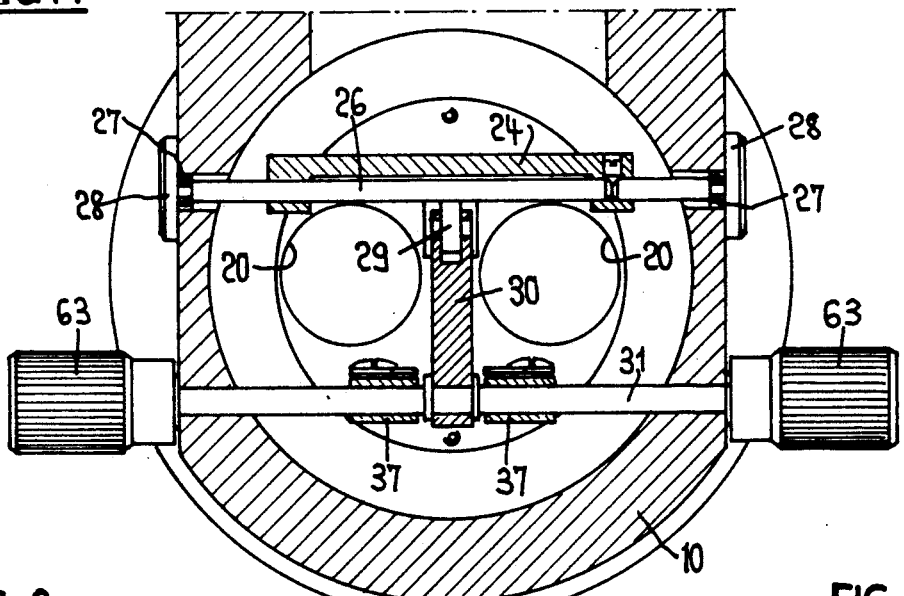
FIG. 7 shows a section according to line VII—VII in FIG. 3.

(FIG. 7). The bearing bores are covered by caps 28 which are fixed on the outside of the housing wall in a not detailedly represented manner. In the horizontal rest position of the mirror 22 and its holder 24 as illustrated in FIGS. 3 and 7, the observation ray beams 21 can pass unrestrained, which appears especially clearly in FIG. 7. A good observation of the eye 4 is therefore possible since all the light entering the lens of the microscope is available for observation.

Mirror 22, respectively its holder 24 is maintained in its position resting against stop pin 41 (FIG. 4) as illustrated in FIGS. 1 and 7, by a leg spring 40. It is engaged from below by a support roller 29 which is rotatably journalled at the top end of an angle lever 30. Angle lever 30 is hinged on an axle 31. In the lower shank of angle lever 30, a roller 32 is journalled which rests on a pin 33 of a control linkage. Pin 33 is disposed in a bushing 34 which is guided in an axially displaceable manner in tube 16. A pressure spring 36 acts between an axially displaceable actuating rod 35 in tube 16 and the bushing 34 and ensures a force-transmitting connection between actuating rod 35 and bushing 34 resp. pin 33. Hence, there is also a force-transmitting, resilient connection between actuating rod 35 and angle lever 30. A drag lever 37, which extends around the lower shank of angle lever 30 in a fork-like manner, is mounted on axle 31. Screwed to drag lever 37 is a leaf spring 38 which is actuated by a driving roller 39 of the lower shank of angle lever 30. A force-transmitting, resilient connection is thus obtained between angle lever 30 and drag lever 37, i.e. when angle lever 30 is pivoted clockwisely from the rest position as shown in FIG. 3 by an upward movement of actuating rod 35 resp. pin 33, drag lever 37 is driven along with a limited momentum which is determined by spring 38. Both levers 30 and 37 are maintained in their shown rest positions by gravity, roller 32 resting on pin 33. In this case, spring 36 is ineffective because bushing 34 abuts to a lock washer 42 at the top end of actuating rod 35.

Figure 8:
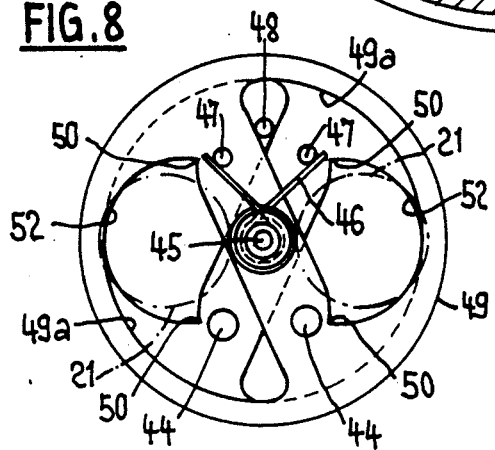
FIG. 8 shows the diaphragm at maximum aperture.
Figure 9:
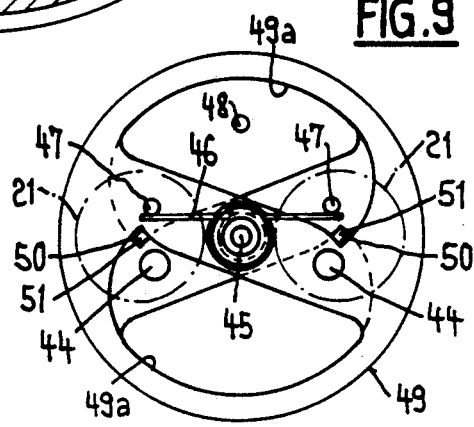
FIG. 9 shows the diaphragm at minimum aperture.

With its horizontal, straight edge 43, drag lever 37 engages two driving rollers 44, each of which is journalled in a diaphragm disk 49.. The two diaphragm disks 49 are hinged on a common axle 45, and the free ends of a spring 46 act upon pins 47 each of which is inserted into a diaphragm disk in order to hold the diaphragm disks in their rest positions in which, according to FIGS. 3 and 8, drag lever 37 does not act upon driving pins 44. This rest position of the diaphragm disks is actually determined by a common stop pin 48. Each diaphragm disk 49 is provided with two symmetrically opposing, approximately semicircular windows 49a. One respective end of the rectilinear portion of the window boundary is bent outwardly, thereby forming window corners 50 which are drawn outwards and which form the diaphragm openings 51 in the case of minimum diaphragm aperture according to FIG. 9. These diaphragm openings extend nearly axialsymmetrically with respect to the beam path 21 which is also indicated in FIGS. 8 and 9. In the rest position according to FIGS. 3 and 8, the diaphragms are fully open and form diaphragm openings 52 which are largely axialsymmetrical with respect to the ray beams 21 as well. In the rest position, i.e. in the observation position, the diaphragms are therefore fully open, and they allow a substantially unrestrained passage of the observation ray beams 21.

FIG. 2 shows the lower end of tube 16 and the actual control device of the photo supplement which is connected thereto. Actuating lever 17 is hinged on an axle 55 in support 53 which is fixed to the lower end of tube 16. In the fork-shaped upper part of this actuating lever 17, a block 56 is pivotably connected to lever 17 by means of a pin 57. The lower end of actuating rod 35 is screwed to this block, and the exact axial position of the latter with respect to actuating lever 17 can be precisely adjusted by rotation of rod 35. Also connected to actuating lever 17 are sockets 58 for coupling at least one triggering cable 18 for a camera. Wire 18a of the triggering cable 18 is engaged in one of two conical recesses 54 of support 53.

In order to take a picture of the observed eye 4, it is sufficient for the observer to press actuating lever 17 to the left in FIGS. 1 and 2, whereby it is tilted clockwisely. Actuating rod 35 is thereby pushed upwards in tube 16 and actuates bushing 34 via spring 36 as well as roller 32 of angle lever 30 by pin 33 and pivots angle lever 30 clockwisely. Roller 29 of angle lever 30 thereby impinges upon the downward-drawn flange 24a of holder 24 for mirror 22 and swivels this holder with the mirror in the counterclockwise direction around axle 26 to the tilted position shown in FIG. 4, in which the holder of the mirror abuts to a lower stop pin 41a. The pivot movement of angle lever 30 and the upward motion of pin 33 and bushing 34 are thus limited, and a further upward movement of actuating rod 35 is absorbed by spring 36 which in this manner represents a force-transmitting, resilient connection between actuating rod 35 respectively actuating lever 17 and angle lever 30. Mirror 22 is now in its effective position in which the ray beam is deflected upwardly into photo tube 13 and to camera 14 according to FIG. 4. When angle lever 30 is pivoted, drag lever 37 is drawn along by spring 38, namely up to a position in which an adjustable stop screw 37a abuts to a polygonal abutment member 60. During its pivot movement to the stop, drag lever 37 actuates the driving pins 44 of the two diaphragm disks 49 and twists the latter against the action of spring 46 until they are in a diaphragm setting which is determined by adjustable abutment member 60. Meanwhile, the diaphragms are placed in a favorable location between mirror 22 and magnification changer 7 of the microscope, i.e. in front of the mirror and more particularly in front of photo tube 13 with respect to the beam path. This results in the already mentioned advantageous conditions for photographic exposures. The strokes are calculated in such a manner that the pivot movement of drag lever 37 is always terminated by a stop before the pivot movement of angle lever 30 is completed. Again, the difference of motion is compensated by the force-transmitting but resilient connection by means of leaf spring 38. Release of the camera 14 is adjusted in such a manner that it takes place only after mirror 22 and drag lever 37 have been pivoted to their respective abutment positions, i.e. when mirror 22 has attained its correct position according to FIG. 4 and the diaphragm has reached the desired aperture. Afterwards, camera 14 is triggered with an appropriate delay as actuating lever 17 is moved further. The flashlight 5a is also activated in the right moment by an electronic device, which is not shown, and a cable 5a. Afterwards, when actuating lever 17 is released, all moving parts return to their rest positions according to FIGS. 3, 7, and 8 due to spring tension or gravity, respectively.

Figure 6:
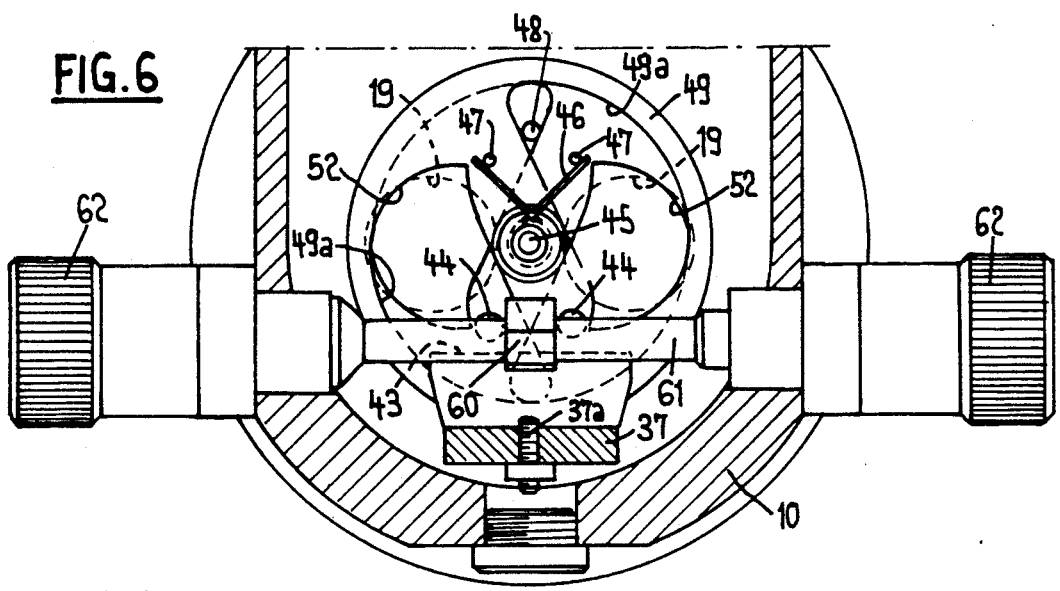
FIG. 6 shows a section according to line VI—VI in FIG. 3.

As shown in FIG. 6, abutment member 60 is mounted on an axle 61 provided with control knobs 62 at its ends.

The position of abutment member 60 and thus the diaphragm aperture can be set by means of these knobs using a scale which is not shown. The positions may be determined by notches.

Drag lever 37 is rigidly connected to axle 31 which has operating knobs 63 mounted on its outer ends. By means of these knobs, the drag lever can be pivoted during observation in order to shut the diaphragm to its preselected aperture. This allows making sure through the oculars that no elements in front of the microscope lens, e.g. parts of the slit illumination, cause any disturbing shades and cut the photo ray beam.

All essential parts of the photo supplement are exchangeable. For example, housing 10 is exchangeably inserted between the magnification changer and the ocular tube of the microscope. Thus it is also possible, in particular, to equip an existing microscope with the photo supplement very easily. A particular simplification is obtained by the fact that all parts of the supplement are connected to housing 10, i.e. only the housing needs to be inserted into the microscope. The photo tube 13 is also removably connected to both the housing 10 and to the camera. This means that different photo tubes and cameras 14 may be used in conjunction with housing 10. In the present case it is assumed that only one ray beam is used in the photo tube 13 and the camera 14 in order to take a mono picture. However, a corresponding arrangement for the production of stereo or instant exposures can be mounted as well. Accordingly, the actuating device of FIG. 2 is intended for different situations, i.e. the releasing cable 18 may optionally be connected to one or the other socket 58 in order to obtain a shorter or longer actuating stroke. Instead of the polygonal abutment member 60, an eccentric disk might be provided in order to allow a continuous diaphragm adjustment.

However, actuation of all components could also be obtained in another manner. For example, it would be conceivable to effect the described movements by means of electromagnets and similar control means using a push-button, the correct chronological sequence possibly being controlled electronically.

Figure 4:
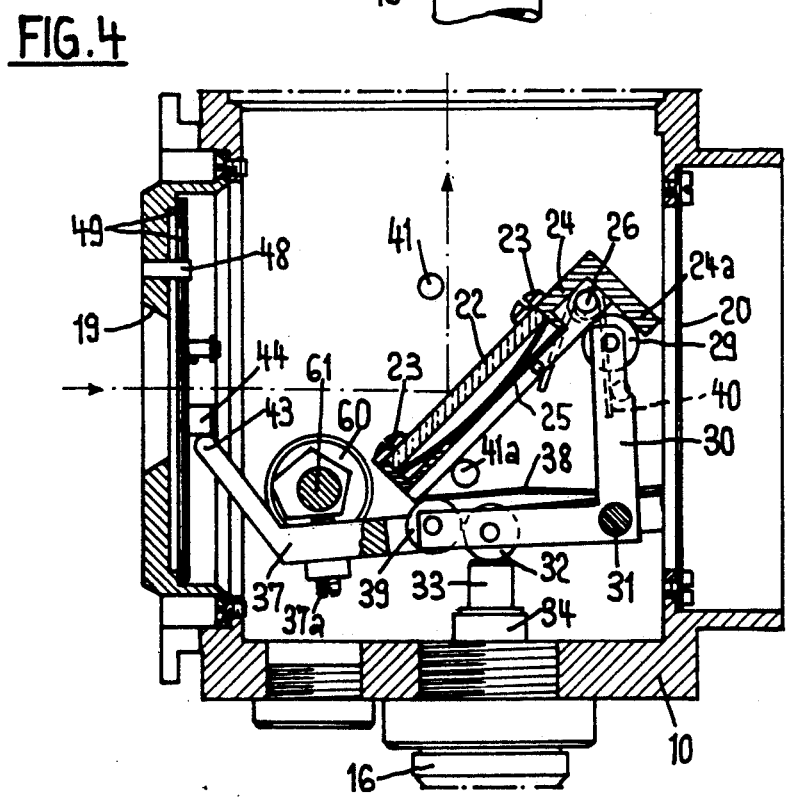
FIG. 4 shows a somewhat simplified section according to FIG. 3 with the mirror and the diaphragm in their working position.
Figure 10:
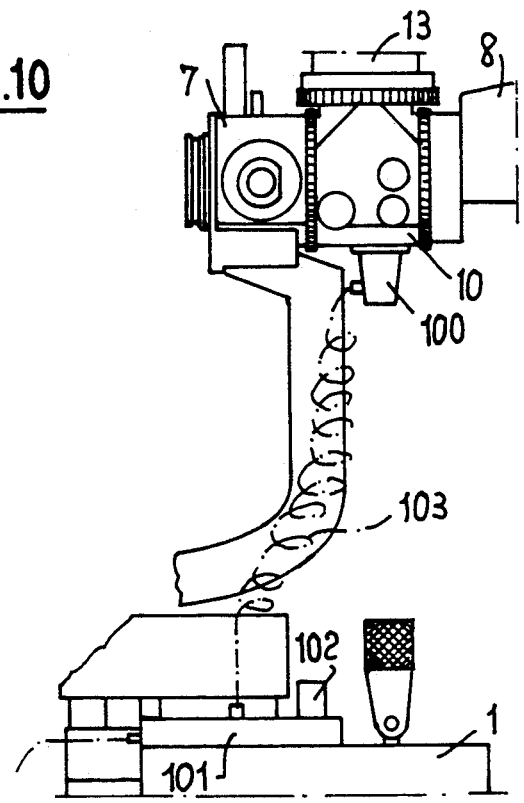
FIG. 10 is a partial view of an alternative embodiment.
Figure 11:
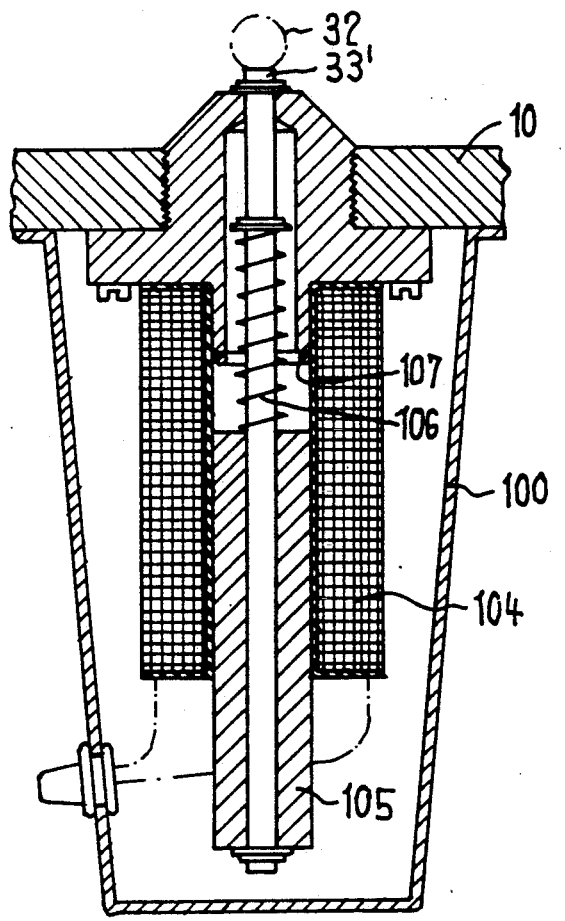
FIG. 11 shows a partial section of said alternative embodiment.

An alternative embodiment of this kind is illustrated in FIGS. 10 and 11. Corresponding parts of FIG. 10 are referenced as in the other figures. Instead of the mechanism for the actuation of mirror 22, an actuating magnet is provided of which only the container 100 is shown in FIG. 10. A box 101 containing the electric equipment and having a release button 102 is mounted on base 1. Connected to terminals of box 101 are a wire 103 for the excitation of magnet 100 and at least another wire for control of the camera and the flashlight. FIG. 11 shows the coils 104 and the plunger 105 of the electromagnet. The plunger 105 is movably disposed on a rod 33' which corresponds to rod 33 and the upper end of which acts upon roller 32 of the tilting arrangement for mirror 22 in such a manner as illustrated in FIGS. 3 and 4. The movement of plunger 105 is transmitted by a spring 106 to rod 33' in order to obtain a force-transmitting actuation of the mirror. An O-Ring 107 serves to prevent a striking impact of plunger 105 upon its abutment.

The operation of the embodiment according to FIGS. 10 and 11 largely corresponds to the described operation of the embodiment of FIGS. 1 to 9 with the difference that all component parts are controlled electrically. When the release button 102 is pressed, the electromagnet 104,104 is excited without any delay, and mirror 22 is tilted in the described manner. After a suitable delay, camera 14 is released via a wire which is not shown and the flashlight is released by wire 5b. However, a control contact could as well be provided which is actuated when mirror 22 has reached its inclined position as required for the exposure, and release of the camera and the flashlight can be controlled by this contact. Stop pin 41a can be conformed as a contact, for example. The flashlight can be released by the camera in the known manner.

We claim:

1. A photo supplement for a microscope having a beam path for observation of an object, comprising: a photographic camera; a fully reflecting mirror adapted to be moved from a first position out of the beam path into a second position into said beam path for deviating light from said beam path into said camera for taking photographic pictures; at least one adjustable diaphragm for controlling the light intensity in said beam path; common actuating means for said mirror, said diaphragm and said camera for simultaneously displacing said mirror, adjusting said diaphragm and triggering said cameras; and first and second stops corresponding respectively to said first and second positions; said actuating means including an actuating member and a spring for moving said mirror from said first position to said second position.

2. A photo supplement according to claim 1, characterized in that the actuating member acts upon the triggering of the camera with a delay.

3. A photo supplement for a microscope having a beam path for observation of an object, comprising: a photographic camera; a fully reflecting mirror adapted to be moved into said beam path for deviating light from said beam path into said camera for taking photographic pictures; at least one adjustable diaphragm adjustable from a first position to a second position for controlling the light intensity in said beam path; an adjustable stop for determining the second position of said diaphragm; and common actuating means for said mirror, said diaphragm and said camera for simultaneously displacing said mirror, adjusting said diaphragm and triggering said camera; said actuating means including an actuating member and a spring for moving said diaphragm means from said first to said second position.

4. A photo supplement for a microscope having a beam path for observation of an object, comprising: a photographic camera; a fully reflecting mirror adapted to be moved into said beam path for deviating light from said beam path into said camera for taking photographic pictures; at least one adjustable diaphragm for controlling the light intensity in said beam path; common actuating means for said mirror, said diaphragm and said camera for simultaneously displacing said mirror, adjusting said diaphragm and triggering said camera; and means for adjusting the diaphragm independently of the mirror.

5. A photo supplement for a microscope having a beam path for observation of an object, comprising: a photographic camera; a fully reflecting mirror adapted to be moved into said beam path for deviating light from said beam path into said camera for taking photographic pictures, at least one adjustable diaphragm for controlling the light intensity in said beam path; common actuating means for said mirror, said diaphragm and said camera for simultaneously displacing said mirror, adjusting said diaphragm and triggering said camera; and selectively mounted lens cones for enabling different type of pictures to be taken.

6. A photo supplement for a microscope having a beam path for observation of an object, comprising: a photographic camera; a flash light; a fully reflecting mirror adapted to be moved into said beam path for deviating light from said beam path into said camera for taking photographic pictures; at least one adjustable diaphragm for controlling the light intensity in said beam path; common actuating means for electromechanically moving said mirror adjusting said diaphragm, triggering said camera, and actuating said flashlight, said actuating means including an electromagnetic for moving said mirror.

7. A photo supplement according to claim 6, characterized in that with respect to the activation of the mirror, the release of the camera and the optional flashlight is electrically delayed or effected by a detector switch which responds in the effective position of the mirror.

8. A photo supplement for a microscope having a beam path for observation of an object, comprising: a photographic camera; a fully reflecting mirror adapted to be moved into said beam path for deviating light from said beam path into said camera for taking photographic pictures; adjustable diaphragm means for controlling the light intensity in said beam path; and common actuating means for said mirror and said diaphragm means for simultaneously displacing said mirror and adjusting said diaphragm means for taking a photographic picture.

9. A photo supplement according to claim 8, characterized in that the diaphragm(s) are placed in front of the mirror with respect to the beam path.

10. A photo supplement according to claim 8, wherein the common actuating means triggers the camera.

11. A photo supplement according to claim 8, wherein the diaphragm means includes two pivotable diaphragm disks each of which is provided with two approximately semicircular windows of the same kind and which are pivotable in opposite directions in a range in which together they form openings which extend substantially symmetrically with respect to the optical axes of the binocular beam paths.

12. A photo supplement according to claim 11, in which at least one return spring maintains the two diaphragm disks in an end position which is determined by a stop and a common actuating member acting upon a respective driving member of each diaphragm disk is provided.

13. An arrangement according to claim 12, in which the approximately semicircular diaphragm windows are extended outwardly at one end of their rectilinear portions, the window corners which are thereby formed and which are drawn outwards determining the smallest diaphragm apertures.

14. A diaphragm arrangement in a binocular microscope having a beam path for observation of an object comprising two pivotable diaphragm disks each of which is provided with two approximately semicircular windows of the same kind and which are pivotable in opposite directions in a range in which together they form openings which extend substantially symmetrically with respect to the optical axes of the binocular beam paths.

15. An arrangement according to claim 14, characterized in that at least one return spring maintains the two diaphragm disks in an end position which is determined by a stop, and in that a common actuating member acting upon a respective driving member of each diaphragm disk (49) is provided.

16. An arrangement according to claim 14, characterized in that the approximately semicircular diaphragm windows are extended outwardly at one end of their rectilinear portions, the window corners which are thereby formed and which are drawn outwards determining the smallest diaphragm apertures.

* * * * *